United States Patent
Wang

(10) Patent No.: US 10,932,944 B2
(45) Date of Patent: Mar. 2, 2021

(54) PORTABLE HEAT GENERATING BANDAGE

(71) Applicant: Pai-Sheng Wang, New Taipei (TW)

(72) Inventor: Pai-Sheng Wang, New Taipei (TW)

( * ) Notice: Subject to any disclaimer, the term of this patent is extended or adjusted under 35 U.S.C. 154(b) by 269 days.

(21) Appl. No.: 15/859,420

(22) Filed: Dec. 30, 2017

(65) Prior Publication Data
US 2019/0201235 A1 Jul. 4, 2019

(51) Int. Cl.
*A61F 7/02* (2006.01)
*A61F 7/00* (2006.01)
*H01M 2/10* (2006.01)

(52) U.S. Cl.
CPC ............... *A61F 7/02* (2013.01); *A61F 7/007* (2013.01); *A61F 2007/008* (2013.01); *A61F 2007/0071* (2013.01); *A61F 2007/0078* (2013.01); *A61F 2007/0088* (2013.01); *A61F 2007/0093* (2013.01); *A61F 2007/0228* (2013.01); *A61F 2007/0231* (2013.01); *H01M 2/1022* (2013.01); *H01M 2220/30* (2013.01)

(58) Field of Classification Search
None
See application file for complete search history.

(56) References Cited

U.S. PATENT DOCUMENTS

| | | | | |
|---|---|---|---|---|
| 5,891,189 | A * | 4/1999 | Payne, Jr. | A61F 7/007 165/46 |
| 8,579,953 | B1 * | 11/2013 | Dunbar | A61F 7/00 607/96 |
| 2002/0165472 | A1 * | 11/2002 | Augustine | A61F 7/007 602/2 |
| 2014/0316494 | A1 * | 10/2014 | Augustine | H05B 3/342 607/112 |
| 2016/0213509 | A1 * | 7/2016 | Petitt | A61F 7/02 |
| 2018/0021167 | A1 * | 1/2018 | Fernandez, Sr. | A61F 7/007 607/100 |
| 2018/0280190 | A1 * | 10/2018 | Betkowski | A41D 13/0051 |

* cited by examiner

*Primary Examiner* — Joseph A Stoklosa
*Assistant Examiner* — Adam J Avigan
(74) *Attorney, Agent, or Firm* — Muncy, Geissler, Olds & Lowe, P.C.

(57) ABSTRACT

A portable heat generating bandage, which includes an elastic bandage provided with a heat generating section, elastic sections, first fixing portions, and second fixing portions; a heat generating unit that is disposed within the heat generating section and used to produce heat energy; a control unit that is electrically connected to the heat generating unit; and a power supply unit that is electrically connected to the control unit and supplies the heat generating unit with electric power required to produce heat energy, thereby facilitating use of the elastic bandage to be worn on a position on the human body. The heat generating unit produces heat energy that is conducted toward the position of the human body to bring about a heat treatment effect. Moreover, the power supply unit is directly fitted on the elastic bandage, thus providing the heat generating bandage with convenience of portability.

2 Claims, 3 Drawing Sheets

PORTABLE HEAT GENERATING BANDAGE

FIELD OF THE INVENTION

The present invention relates to a heat generating bandage, and in particular embodiments to a heat generating bandage with use as wearable device on a position on the human body to bring about a heat treatment effect and that is easily carried.

BACKGROUND

The majority of early heat therapy or light therapy products are of plastic hand-hold types, and, moreover, are generally designed to suit each position of the human body, thus limiting the operational degree of freedom the user has. And even though such products are designed to suit each body position, however, because body type and size of different users vary, thus, the needs of users cannot be met by such products. In addition, these types of products generally use a mobile power supply, making it inconvenient to use, and having the consumer bear the cost.

Accordingly, the problem to be solved by the present invention involves providing a heat generating bandage that is easily carried.

SUMMARY

An objective of the bandages disclosed herein lies in providing a heat generating bandage, and more particularly to a heat generating bandage with use as wearable device on a position on the human body to bring about a heat treatment effect and that is easily carried.

In one way to achieve the aforementioned objective, the heat generating bandage comprises an elastic bandage, a heat generating unit, a control unit, and a power supply unit. The elastic bandage comprises a heat generating section provided with a heat generating surface, at least one elastic section located on an end edge of one side of the heat generating section and provided with an elastic expansion-contraction characteristic, at least one first fixing portion located at the elastic section relatively positioned to the heat generating section, and a second fixing portion located at the heat generating section relative to the heat generating surface and securely fastened together with the first fixing portions.

In some embodiments, the heat generating unit is disposed within the heat generating section and used to produce heat energy. The control unit is fitted on the elastic bandage and is electrically connected to the heat generating unit to control the switching on/off of the heat generating unit. The power supply unit is electrically connected to the control unit, and supplies the heat generating unit with electric power required to produce heat energy.

In one embodiment, the elastic bandage further comprises two of the elastic sections and two of the first fixing portions, wherein the two elastic sections are respectively located on the end edges of the two sides of the heat generating section, and the two first fixing portions are respectively located at the two elastic sections at positions relative to the heat generating section.

In one embodiment, the two first fixing portions and the second fixing portion are respectively hook-and-loop fastener strips that can hook-and-loop fasten together.

In one embodiment, the power supply unit is a rechargeable battery pack.

In one embodiment, the control unit further comprises a power supply cable electrically connected to the power supply unit.

In one embodiment, one end of the power supply cable is electrically connected to the control unit, and the other end is provided with a first connecting portion that is electrically connected to the power supply unit. And the power supply unit further comprises a second connecting portion to enable the first connecting portion to insert and connect therein.

In one embodiment, the heat generating unit is a heating wire able to emit infra-red rays.

In one embodiment, the heat generating section further comprises a retaining space used to retain the power supply unit.

The disclosed bandages have the following advantages over prior known devices:

1. The power supply unit is fitted on the elastic bandage, enabling convenient carrying.
2. The elastic sections are provided on the elastic bandage, and the elastic expansion-contraction characteristic of the elastic sections enables achieving adjusting an appropriate tightness on a position on the human body, thereby increasing comfortability when wearing.

To enable a further understanding of said objectives and the technological methods herein, a brief description of the drawings is provided below followed by a detailed description of the preferred embodiments.

DETAILED DESCRIPTION OF THE EMBODIMENTS

Figure 1:
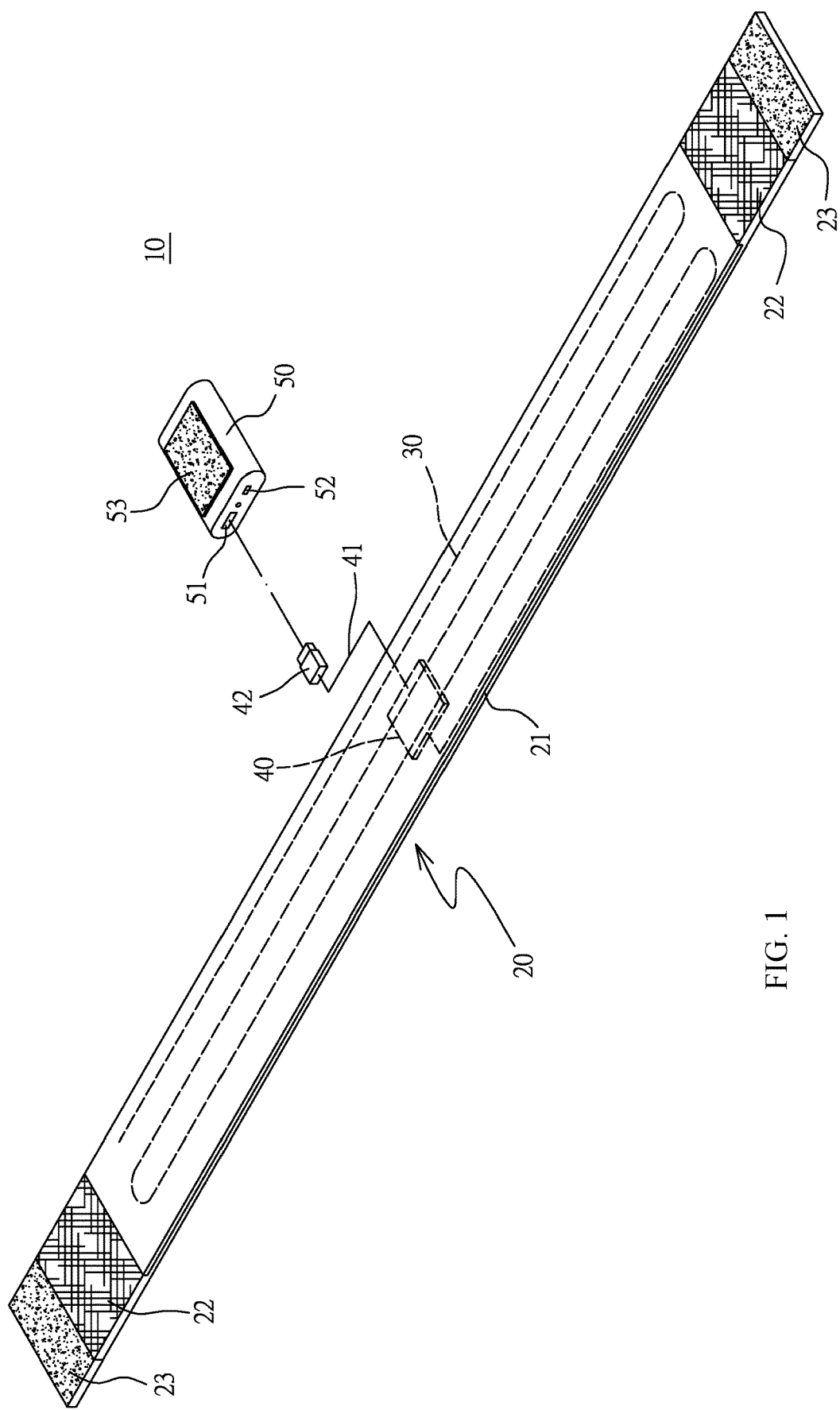
FIG. 1 is an elevational schematic view when opened up.
Figure 2:
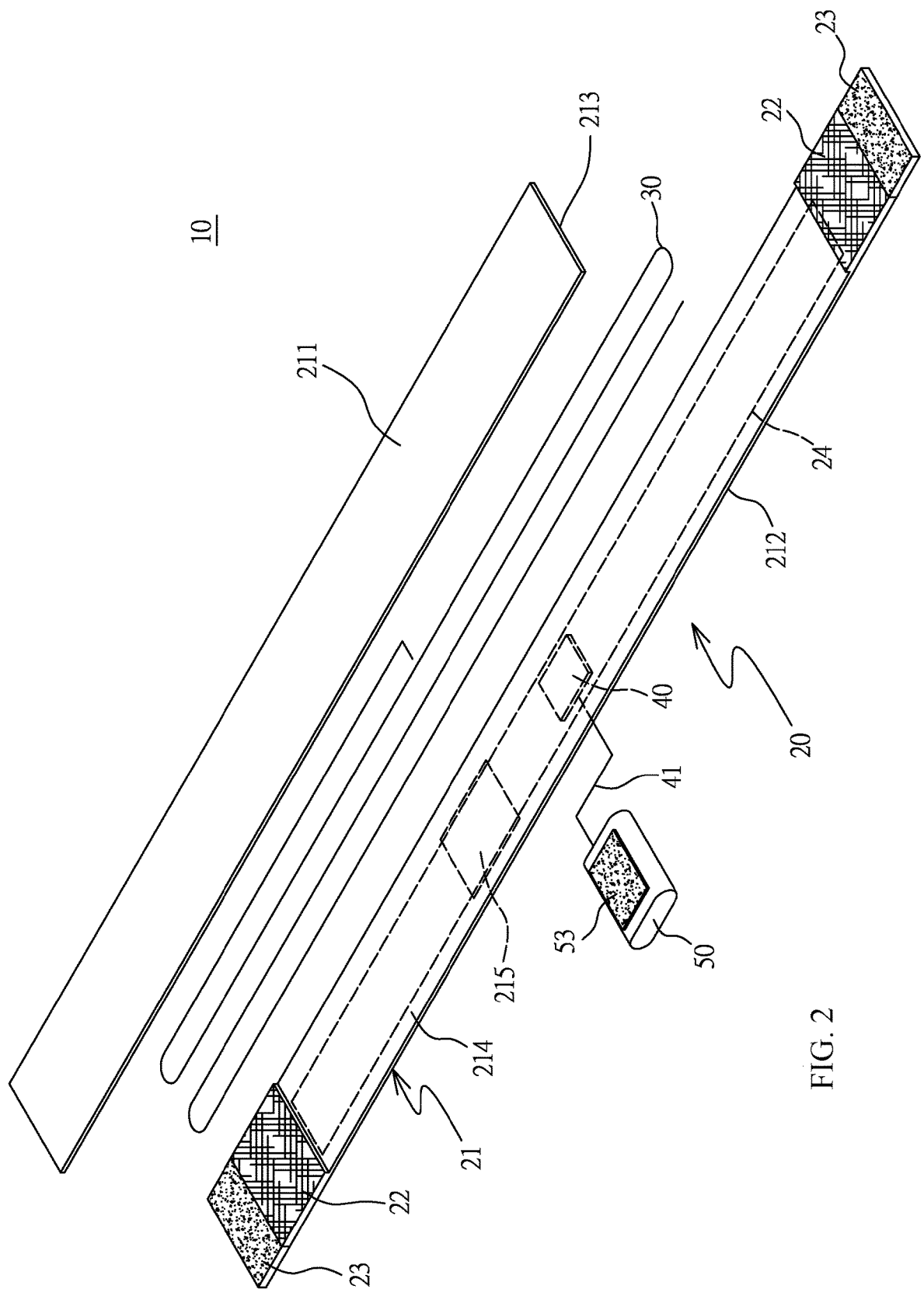
FIG. 2 is an exploded schematic view when opened up.

Referring to FIG. 1 and FIG. 2, which show a heat generating bandage 10 with use as a wearable device on a position on the human body, such as the waist, a leg, a shoulder. The heat generating bandage 10 comprises an elastic bandage 20, a heat generating unit 30, a control unit 40, and a power supply unit 50.

The elastic bandage 20 comprises a heat generating section 21, at least one elastic section 22, at least one first fixing portion 23, and at least one second fixing portion 24. In the present embodiment, the configuration comprises two of the elastic sections 22 and two of the first fixing portions 23. The heat generating section 21 is made from soft, flexible material, thereby providing the heat generating section 21 with flexibility. The top portion is provided with a heat generating surface 211 and a rear surface 212 corresponding to the heat generating surface 211. In the present embodiment, the heat generating section 21 is assembled from a superposition of a first portion 213 and a second portion 214, with the heat generating surface 211 located on the first portion 213. The rear surface 212 is located on the surface of the second portion 214 corresponding to the first portion 213, and a retaining space 215 used to retain the power supply unit 50 is further provided on the rear surface 212. The two elastic sections 22 are respectively disposed on two corresponding sides of the heat generating section 21, and respectively connected to the heat generating section 21.

In certain embodiments, each of the elastic sections 22 are made from elastic material, thereby respectively providing each of the elastic sections 22 on the two corresponding sides of the heat generating section 21 with an elastic expansion-contraction characteristic. The two first fixing portions 23 are respectively located on corresponding sides of the two elastic sections 22 relative to the heat generating section 21; moreover, each of the first fixing portions 23 is connected to the respective elastic section 22. The second fixing portion 24 is disposed on the rear surface 212 of the heat generating section 21. In the present embodiment, the first fixing portions 23 and the second fixing portion 24 are respectively hook-and-loop fastener strips that can mutual hook-and-loop fasten together.

The heat generating unit 30 is disposed within the heat generating section 21, and located between the first portions 213 and the second portions 214. The heat generating unit 30 is used to emit heat energy, and causes the heat energy to be conducted outwardly from the first portion 213, thereby enabling the heat generating surface 211 located on the first portion 213 to release the heat energy. In the present embodiment, the heat generating unit 30 is a heating wire, which is used to emit far infrared rays. The heat generating unit 30 is made from a soft, flexible material and thus provided with flexibility similar to the heat generating section 21, enabling flexible deformation thereof along with shaping the elastic bandage 20 to fit a body portion. Apart from being a heating wire, it is understood that the heat generating unit 30 can also use any material capable of emitting heat energy, such as a flexible LED (Light Emitting Diode) light strip.

The control unit 40 is disposed on the elastic bandage 20. In the present embodiment, the control unit 40 is disposed on the rear surface 212 of the heat generating section 21, and further electrically connected to the heat generating unit 30 to control the switching on/off operation of the heat generating unit 30. In addition, a power supply cable 41 also extends from the control unit 40, with one end of the power supply cable 41 electrically connected to the control unit 40, and a first connecting portion 42 provided on the other end.

The power supply unit 50 is used to electrically connect to the control unit 40, and also provides the heat generating unit 30 with electric power required to produce heat energy. In the present embodiment, the power supply unit 50 uses the power supply cable 41 to electrically connect to the control unit 40. The power supply unit 50 is a rechargeable battery pack, and a second connecting portion 51 is provided on the power supply unit 50 to enable inserting the first connecting portion 42 therein. Moreover, a third connecting portion 52 is further provided on the power supply unit 50, and the third connecting portion 52 is used to electrically connect to an external power source.

In some embodiments, the external power source is used to recharge the power supply unit 50. In the present embodiment, the described first connecting portion 42 and the second connecting portion 51 are a pair of USB (Universal Serial Bus) connectors providing mutual connectivity, and the described third connecting portion 52 is a C TYPE connector or a TYPE C connector, which increases applicability of the power supply unit 50. Furthermore, a third fixing portion 53 is further disposed on the power supply unit 50, with the third fixing portion 53 enabling secure fastening together with the second fixing portions 24. The third fixing portion 53 and the second fixing portion 24 are similarly hook-and-loop fastener strips that can mutual hook-and-loop fasten together.

Accordingly, when using the heat generating bandage 10, the elastic bandage 20 is first wound around onto a position on the human body, causing the heat generating surface 211 to cling closely to the position of the human body. After winding the elastic bandage 20 around onto the position of the human body, the first fixing portions 23 are then used to mutually fasten to the second fixing portion 24, thereby ensuring the elastic bandage 20 does not come away from the portion of the human body. The control unit 40 is then electrically connected to the second connecting portion 51 of the power supply unit 50 using the first connecting portion 42, thereby providing power to the control unit 40, and the power supply unit 50 is securely fastened to the second fixing portion 24 using the third fixing portion 53, or the power supply unit 50 is retained inside the retaining space 215, thereby securely fastening the power supply unit 50 on the elastic bandage 20. Accordingly, the user is able to activate operation of the heat generating unit 30 through the control unit 40 to cause the heat generating surface 211 to produce heat energy, which is directed toward the position on the human body to bring about a heat treatment effect.

In certain embodiments, the elastic bandage 10 is wound around onto the position on the human body, the user is able to use the elastic expansion-contraction characteristic on the two sides of the heat generating section 21 to adjust tightness of the elastic bandage 20 wound around the body position. Moreover, because the elastic bandage 20 and the heat generating unit 30 are similarly made from soft, flexible material, they are provided with flexibility, hence, when wound around onto the body position, the elastic bandage 20 is able to achieve close contact with the body position. In addition, during the process of winding round the elastic bandage 20 onto the body position, the user is further able to avoid the wounded area on the body position and carry on winding around, thereby the improving the heat treatment effectiveness while preventing causing secondary injury to the wound.

Figure 3:
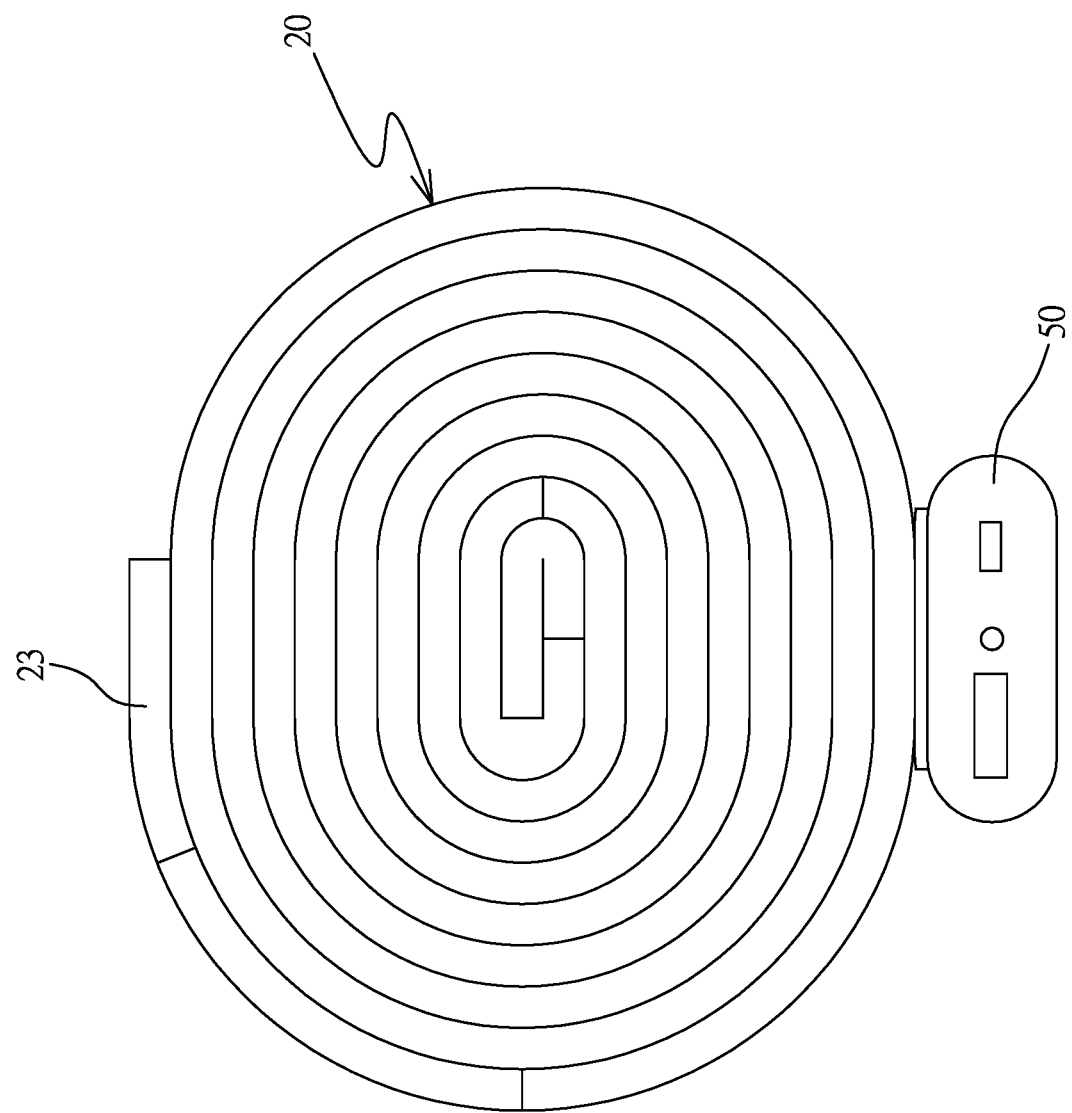
FIG. 3 is a top view when rolled up.

Referring to FIG. 1 to FIG. 3, when storing away the disclosed bandage, the elastic bandage 20 can be rolled up to form a circular form, and then use the first fixing portions 23 to mutually fasten with the second fixing portions 24, thereby enabling the elastic bandage 20 to be effectively securely rolled up. Furthermore, the power supply unit 50 can also be fastened to the second fixing portion 24 using the third fixing portion 53, to securely fasten the power supply unit 50 on the rolled up elastic bandage 20, thus further reducing the stored-away bulk of the entire elastic bandage 20 as well as facilitating portability and storing away.

Compared with the prior art, when wound around onto a position of the human body, the elastic bandage 20 is able to avoid a wounded area on the body position, and prevent causing secondary injury to the wound. Moreover, after the bandage is wound around onto a position of the human body, the configuration of the first fixing portions 23 and the second fixing portion 24 enables quick, secure fastening of the elastic bandage 20, thus improving convenience of use thereof. In addition, the configuration of the elastic bandage 20 enables it to be worn on any body position of the human body, and, moreover, uses the two elastic sections 22 to adjust tightness of the elastic bandage 20 wound around the body position, thus providing more widespread use of the heat generating bandage 10.

It is of course to be understood that the embodiments described herein are merely illustrative of the principles of the invention and that a wide variety of modifications thereto may be effected by persons skilled in the art without departing from the spirit and scope of the invention as set forth in the following claims.

What is claimed is:

1. A portable heat generating bandage, comprising:
   an elastic bandage, the elastic bandage comprises a heat generating section provided with a heat generating surface, at least one elastic section located on an end edge of one side of the heat generating section and provided with an elastic expansion-contraction characteristic, at least one first fixing portion located at the elastic section relatively positioned to the heat generating section, and a second fixing portion located at the heat generating section relative to the heat generating surface and securely fastened together with the first fixing portion;

a heat generating unit, the heat generating unit is disposed within the heat generating section;

a control unit, the control unit is fitted on the elastic bandage and is electrically connected to the heat generating unit to control the switching on or off of the heat generating unit; and a power supply unit, the power supply unit is electrically connected to the control unit, and supplies the heat generating unit with electric power required to produce heat energy, wherein the elastic bandage further comprises two of the elastic sections and two of the first fixing portions, wherein the two elastic sections are respectively located on the end edges of the two sides of the heat generating section, and the two first fixing portions are respectively located at the two elastic sections at positions relative to the heat generating section, wherein the two first fixing portions and the second fixing portion are respectively hook-and-loop fastener strips that can hook-and-loop fasten together, wherein the power supply unit is a rechargeable battery pack, wherein the power supply unit further comprises a third fixing portion, with the third fixing portion able to secure fastening together with the second fixing portions, wherein the control unit further comprises a power supply cable that is electrically connected to the power supply unit, wherein one end of the power supply cable is electrically connected to the control unit, the other end is provided with a first connecting portion that is electrically connected to the power supply unit, and the power supply unit further comprises a second connecting portion to enable the first connecting portion to insert and connect therein, and wherein the heat generating unit is a heating wire able to emit infra-red rays.

2. The portable heat generating bandage according to claim 1, wherein the heat generating section further comprises a retaining space used to retain the power supply unit.

* * * * *